US 8,926,593 B2

(12) United States Patent
Croizat et al.

(10) Patent No.: US 8,926,593 B2
(45) Date of Patent: Jan. 6, 2015

(54) WOUND SUPPORT FOR USE IN VACUUM THERAPY OF WOUNDS

(75) Inventors: Pierre Croizat, Herbrechtingen (DE); Axel Eckstein, Heidenheim (DE)

(73) Assignee: Paul Hartmann AG, Heidenheim (DE)

( * ) Notice: Subject to any disclaimer, the term of this patent is extended or adjusted under 35 U.S.C. 154(b) by 168 days.

(21) Appl. No.: 13/602,345

(22) Filed: Sep. 4, 2012

(65) Prior Publication Data

US 2013/0066286 A1    Mar. 14, 2013

Related U.S. Application Data

(60) Provisional application No. 61/573,185, filed on Sep. 21, 2011.

(30) Foreign Application Priority Data

Sep. 8, 2011    (DE) .......................... 10 2011 082 347

(51) Int. Cl.
*A61M 1/00*    (2006.01)

(52) U.S. Cl.
CPC ........... *A61M 1/0088* (2013.01); *A61M 1/0084* (2013.01)
USPC ............ 604/543; 604/313; 604/317; 604/319

(58) Field of Classification Search
CPC ........................... A61M 1/0088; A61M 1/0084
USPC .......... 604/313, 304, 305, 317–327, 354, 543
See application file for complete search history.

(56) References Cited

U.S. PATENT DOCUMENTS

| 4,232,129 | A * | 11/1980 | Gibbs et al. ................... | 521/137 |
| 2004/0106703 | A1* | 6/2004 | Etzrodt et al. ................. | 523/330 |
| 2006/0100586 | A1* | 5/2006 | Karpowicz et al. ........... | 604/180 |
| 2008/0287892 | A1* | 11/2008 | Khan et al. ..................... | 604/313 |
| 2010/0191197 | A1* | 7/2010 | Braga et al. ..................... | 604/313 |
| 2010/0227939 | A1* | 9/2010 | Mohmeyer et al. ........... | 521/170 |
| 2011/0152800 | A1* | 6/2011 | Eckstein et al. .............. | 604/319 |
| 2012/0101458 | A1* | 4/2012 | Hall et al. ..................... | 604/319 |

FOREIGN PATENT DOCUMENTS

| DE | 20 2004 018 245 | 8/2005 |
| DE | 10 2008 020 553 | 10/2008 |
| DE | 20 2009 016 012 | 3/2010 |
| DE | 20 2010 009 148 | 10/2010 |
| WO | WO 03/057071 | * 7/2003 |

* cited by examiner

*Primary Examiner* — Philip R Wiest
*Assistant Examiner* — Ariana Zimbouski
(74) *Attorney, Agent, or Firm* — Paul Vincent

(57) ABSTRACT

A wound support (50) for use in the vacuum therapy of wounds, can be disposed in its intended use in a wound space underneath a vacuum dressing (6) sealing the wound space with respect to the atmosphere in an essentially vacuum-tight manner, wherein the wound space can communicate with a suction tube (10) to which a vacuum can be applied through an opening (20) in the vacuum dressing (6). The wound support (50) comprises a flexibly compliant foamed material and has a through-hole (54) that extends in the direction of the wound depth, which is used to insert or pass through a wound-side end section (44) of a fluid feed tube (40). A sleeve (56) is disposed in the through-hole (54) into which this end section (44) can be inserted.

16 Claims, 4 Drawing Sheets

WOUND SUPPORT FOR USE IN VACUUM THERAPY OF WOUNDS

This application claims benefit of 61/573,185 filed on Sep. 21, 2011 as well as Paris Convention priority of DE 10 2011 082 347.6 filed on Sep. 8, 2011 the entire disclosures of which are hereby incorporated by reference.

BACKGROUND OF THE INVENTION

The invention relates to a wound support for use in the vacuum therapy of wounds, wherein the wound support can be disposed in its intended use in a wound space underneath a vacuum dressing sealing the wound space with respect to the atmosphere in an essentially vacuum-tight manner, and wherein the wound space can communicate with a suction tube to which a vacuum can be applied through an opening in the vacuum dressing, wherein the wound support comprises a flexibly compliant foamed material. Wound supports for use in the vacuum therapy of wounds have been previously described in e.g. WO 2004/037334 and WO 2010/033272.

The importance of the vacuum therapy of wounds, in particular, of wounds that are deep and whose healing is therefore problematic, has recently grown. Vacuum therapy means that a region of the body or wound that would otherwise be exposed to the atmosphere is pressure-tightly and vacuum-tightly sealed against the environment, that is, the atmosphere in which we live and breathe, by means to be described in more detail below, wherein a pressure that is reduced with respect to atmospheric pressure in a manner still to be described, which is therefore negative pressure with respect to the atmosphere, can be applied and continuously maintained within the sealed wound space. Where mention is made of a vacuum in the area described here, this refers to a pressure range of typically between 0 and 250 mm Hg (mm of mercury) below ambient atmospheric pressure. It has been shown that this is conducive to wound healing. Vacuum-tight sealing can be achieved with a vacuum dressing that, for example, can comprise a pressure-tight or vacuum-tight film layer, which is typically adhesively bonded to an intact region of the body surrounding the wound, thus providing a tight seal. To supply vacuum to the wound space and maintain it there, from a device for producing a vacuum, that is, a vacuum pump in the broadest sense, in the case of the systems stated here for the vacuum therapy of wounds, conduits can be used to which a vacuum is applied that act in conjunction with the vacuum dressing by means of a connecting device to apply a vacuum on or in the wound space.

The objective of this invention is to improve a wound support of the type described above so that it can be used for a broader range of tasks, in particular, for instillation therapy.

SUMMARY OF THE INVENTION

This object is inventively achieved in that the wound support has a through-hole that extends in the direction of the wound depth, which is used to insert or pass through a wound-side end section of a fluid feed tube, and that a sleeve is disposed in the through-hole into which this end section can be inserted.

Because inventively a sleeve is disposed in the through-hole of the foam-based wound support, simple and secure insertion of the wound-facing end section of the fluid feed tube can be ensured. Thus this end section is given a pre-defined orientation in the wound space, without it being necessary for the treating person to perform complicated handling of the tube components in the wound space or inside the wound support when applying the components for the vacuum therapy. Moreover, there is less danger that arranging the components will result in painful discomfort of the patient. It thus proves particularly advantageous that, due to the inventive disposition of the sleeve, the end section of the fluid feed tube does not have to project beyond the side of the wound support facing the wound base, so that irritation of the wound base resulting from the fluid feed tube can be avoided. Even so, according to the invention, it can be ensured that liquid or gaseous media that are conveyed via the fluid feed tube, such as rinsing liquid or oxygen, for example, can be conveyed all the way to the wound base, where they are particularly needed. Because if, for example, rinsing liquid or liquid with pharmaceutically effective substances that support wound healing are only conveyed to a region of the wound support facing away from the wound base to be then immediately suctioned out again through a suction tube, the therapeutic effect of this measure is severely diminished. The inventive wound support, on the other hand, ensures that the conveyed fluid can reach the wound base where it can have its intended therapeutic effect. Even if merely rinsing fluid, for example, in the form of Ringer's solution, is applied, effective rinsing and therefore cleansing of the wound space can be achieved.

The sleeve preferably rests directly against the foamed material of the wound support.

In a further embodiment of the invention, it proves advantageous if the sleeve has a collar at least on one side, preferably on both sides of the foamed material, with which the sleeve rests axially against a side of the foamed material that surrounds the opening with respect to a longitudinal axis of the sleeve. By this means, an even and an edge-free transition from the sleeve to the foamed material of the wound support can be achieved, and insertion of the end section of the fluid feed tube can be implemented more simply. It further proves advantageous if the collar is closed around its entire circumference.

According to a further inventive embodiment of particular significance, it is advantageous if the length of the sleeve can be altered so that the sleeve can be adapted to the compression or contraction of the foamed material of the wound support. For this, the sleeve according to a further inventive idea can have two sliding telescopic sleeve sections that slide toward each other along a sleeve longitudinal axis. According to another inventive idea it is possible for the sleeve to comprise two sleeve sections that can slide toward each other by means of a bellows-type coupling along the sleeve longitudinal axis.

The sleeve can, for example, be made of plastics such as thermoplastics, elastomers, thermoplastic elastomers, or silicone.

The wound support comprises a flexibly compliant foamed material, wherein the foamed material is preferably an open-cell polyurethane foamed plastic (PUR foamed plastic). Foamed plastics usually refer to materials with cells (open, closed, or both) distributed over the entire mass. Such materials therefore usually exhibit a gross density (acc. to DIN EN ISO 845) that is lower than the density of the skeletal substance.

[Cell]

A cell is the individual hollow space formed when foamed materials are manufactured, which is partially or completely surrounded by cell walls and/or cell edges.

[Open-Cell]

A closed cell is usually a cell that is completely enclosed by its walls and does not therefore communicate with the other cells via the gas phase.

An open cell is usually a cell that communicates with other cells via the gas phase. Within the scope of this application, the term open-cell means that the polyurethane foamed plastic contains at least 60% open cells, preferably, at least 90% open cells, more preferably, at least 98% open cells, in particular, essentially 100% open cells, with reference to the total number of cells. The percentage of open cells in the polyurethane foamed plastic is customarily defined according to ASTM D 285687, test method B).

[Tensile Strength]

According to the invention, the polyurethane foamed plastic usually exhibits a tensile strength after three days of storage in bovine serum of between 80 kPa and 300 kPa, preferably, between 110 kPa and 250 kPa, more preferably, between 120 kPa and 230 kPa, even more preferably, between 130 and 220 kPa, especially preferably, between 140 to 200 kPa, highly preferably, between 155 and 190 kPa, and especially, between 160 and 185 kPa.

Bovine serum is known in the specialist field. It is a serum that is extracted from the blood of cattle. Preferably, the bovine serum marketed under the trade name HyClone® "Standard Fetal Bovine Serum" made by the company Thermo Scientific is used. In a preferred embodiment, the bovine serum used essentially has the following composition and properties:

| Protein content and additional values | |
|---|---|
| Albumin | 1.9 gm/dl |
| Alkaline phosphatase | 213 mU/ml |
| Blood urea nitrogen | 12 mg/dl |
| Creatinine | 2.77 mg/dl |
| Gamma globulin | 1.7 % tp |
| Glucose | 107 mg/dl |
| Glutamic oxaloacetic transaminase (SGOT) | 152 mU/ml |
| Glutamic pyruvate transaminase (SGPT) | 37 mU/ml |
| IgG - nephelometer | 0.14 mg/ml |
| Lactate dehydrogenase | 2479 mU/ml |
| Osmolality | 312 mOsm/kg |
| PH | 7.18 |
| Total bilirubin | 0.4 mg/dl |
| Total protein | 3.7 gm/dl |
| Content of trace elements and iron | |
| Calcium | 13.1 mg/dl |
| Chloride | 99 mEq/l |
| Inorganic phosphorous | 9.6 mg/dl |
| Iron | 160 ug/dl |
| Saturation concentration (iron) | 79% |
| Potassium | >10.0 mEq/l |
| Sodium | 133 mEq/l |
| Total iron binding capacity (TIBC) | 201 ug/dl |

The test specimen to be measured is placed and submersed in bovine serum for three days at 23° C. Then, the tensile strength according to DIN 53571 is determined. Within the scope of this application, the expression "according to DIN 53571" means that the tensile strength is always determined according to this standard, wherein, however, contrary to the standard, the test specimen stored in bovine serum for three days is not fully dried. Instead, the test specimen is removed from the bovine serum and submersed in one liter of water to rinse it. Then, the test specimen is squeezed out with wood-free paper. Furthermore, contrary to the standard, a square test specimen of dimensions 10×12.5×75 is used.

The measurement of the tensile strength is performed with a tensile testing machine according to EN ISO 527-1 [April 1996] made by Zwick (Ulm). The following test parameters are used:

Test speed: 500 mm/min
Clamping length: 50 mm
Pre-load: 0.1 N
Test specimen width b0: 12.5 mm.

[Elongation at Break]

Further, the polyurethane foamed plastic preferably exhibits an elongation at break of 150% to 700%, more preferably, of 200% to 650%, even more preferably, of 240% to 340%, especially, of 260 to 320%, measured according to DIN 53571 (method 1, test specimen A). Furthermore, the polyurethane foamed plastic preferably exhibits a Shore A hardness of 20 to 70, even more preferably, of Shore A hardness 40 to 50, measured according to DIN 53505, wherein the measurement was performed at 23° C. on a plate-shaped, even and smooth test specimen with a thickness of 6 mm.

[Air Permeability]

Furthermore, it has been shown that the tasks mentioned above can be solved unexpectedly advantageously if the polyurethane foamed plastic exhibits special air permeability. In a preferred embodiment, the polyurethane foamed plastic exhibits an air permeability of 1000 to 8000 $1/(m^2 \ sec)$, more preferably, of 1500 to 6000 $1/(m^2 \ sec)$, even more preferably, of 2000 to 5000 $1/(m^2 \ sec)$, especially preferably of 2300 to 4000 $1/(m^2 \ sec)$, and especially, of 2400 to 3300 $1/(m^2 \ sec)$, measured according to DIN EN ISO 9237 (20 mm test thickness, 20 $cm^2$ test surface, 200 Pa differential pressure).

[Viscoelastic Properties]

It has also been shown that the tasks mentioned above can be solved unexpectedly advantageously if the polyurethane foamed plastic exhibits viscoelastic properties. This means that polyurethane foamed plastic responds to stress in the same way as the combination of an elastic solid and a viscous liquid. The viscoelastic behavior can be characterized by a torsional vibration test according to DIN 53445, method A. Preferably, for the test according to DIN 53445, test A, the foamed plastic exhibits a mechanical loss factor of 0.1 to 1.0, more preferably, of 0.15 to 0.8, even more preferably, of 0.2 to 0.6.

[Gross Density]

It has also been shown that the tasks described above can be solved unexpectedly advantageously if the foamed plastic exhibits a gross density of between 15 and 55 $kg/m^3$, more preferably, of between 20 and 35 $kg/m^3$, even more preferably, of between 22 and 30 $kg/m^3$, in particular, of between 24 and 28 $kg/m^3$, measured according to DIN EN ISO 845 (test specimen with dimensions of 100 mm×100 mm×50 mm, conditioning for 24 h under standard atmospheric conditions (23° C., 50% rel. air humidity, 1013 mbar)).

Unless otherwise stated in the relevant standards, all test methods are generally performed at 23° C., 50% rel. air humidity and 1013 mbar pressure.

Foamed Plastic—Chemical Composition:

Preferred embodiments of the polyurethane foamed plastics (PUR) are explained below. The polyurethane foamed plastic is usually obtained by the reaction of a mixture that contains the following components (i-PUR) polyisocyanate,
(ii-PUR) compounds that react with isocyanate, in particular, polyol
(iii-PUR), foaming agent,
(iv-PUR), catalyst, and
(v-PUR), if necessary, additives.

Isocyanates (i-PUR) that can be used are generally known aliphatic, cycloaliphatic and/or, in particular, aromatic polyisocyanates. For the production of polyurethane, for example, methylene diphenyl diisocyanate (MDI), here, in particular 4.4'methylene diphenyl diisocyanate (4.4'-MDI), mixtures of monomer methylene diphenyl diisocyanates and higher homologs of methylene diphenyl diisocyanate (PMDI), tetramethylendiisocyanate (TMDI), hexamethylene diisocyanate (HDI), tolylene diisocyanate (TDI), or mixtures thereof.

Preferably MDI, in particular, 4.4' MDI and/or HDI are used. The especially preferred 4.4' MDI can contain small quantities, up to approximately 10% by weight, of allophanate modified or uretonimine modified polyisocyanates. Small quantities of polyphenylene-polymethylene-polyisocyanate (PMDI) can also be used. The total quantity of this PMDI should not exceed 5 percent by weight of the isocyanate use.

The polyisocyanate component (i-PUR) is preferably used in the form of polyisocyanate prepolymers. These polyisocyanate prepolymers are obtained by converting polyisocyanates (i-PUR) described above, for example, at temperatures of 30 to 100° C., preferably, at approximately 80° C., with an insufficient amount of the polyols (i-PUR), described below, to prepolymer. The polyol-polyiscyanate ratio is chosen such that the NCO content of prepolymers is 8 to 28% by weight, preferably, 14 to 26% by weight, especially preferably, 17 to 23% by weight.

Usually, polyols such as polyetherol and/or polyesterol are the compounds used that react with isocyanates (ii-PUR).

Polyether polyalcohols (referred to as "polyether polyols" in this application) with an OH functionality of 1.9 to 8.0, a hydroxyl number of 50 to 1000 mg KOH/g and, if necessary, 10 to 100% of primary hydroxyl groups can be used. Such polyether polyols are known, commercially available, and are based, for example, on initiator compounds that are converted with alkylene oxides, for example, propylene oxide and/or ethylene oxide, under generally known conditions. The content of primary hydroxyl groups can be achieved by reacting the polyols with ethylene oxide at the end. Preferably, no polyether polyols are used in the production of the open-cell foamed plastic (c).

Preferably, polyester polyols are used in the component (ii-PUR). The polyesterols (ii-PUR) used are generally manufactured by condensing polyfunctional alcohols, preferably diols, with 2 to 12 carbon atoms, preferably, 2 to 6 carbon atoms, with polyfunctional carboxylic acids with 2 to 12 carbon atoms, preferably 4 to 8 carbon atoms. Examples of suitable acids are succinic acid, glutaric acid, adipic acid, phthalic acid, isphthalic acid, and/or terephthalic acid and mixtures thereof. Adipic acid is especially preferred. Examples of suitable two and dihydric and polyhydric alcohols are ethandiol, diethylene glycol, butandiol-1,4, pentandiol-1,5, and/or hexandiol-1,6 and mixtures thereof. Butandiol-1,4 is especially preferred.

The reaction conditions for carboxylic acid and alcohol are usually chosen such that the resulting polyesterols do not have any free acid groups. Furthermore, the resulting polyesterols generally exhibit a weight-averaged molecular weight (determined by means of gel permeation chromatography) of 500 to 3500 g/mol, preferably, of more than 1000 g/mol to 3000 g/mol, in particular, of 1500 to 2400 g/mol. Generally, the polyesterols used exhibit an average theoretical functionality of 2.0 to 4, possibly, of more than 2 to less than 3. Furthermore, in general, the polyesterols used exhibit an average OH number of 20 to 150, preferably 30 to 80.

In a preferred embodiment, the polyesterols used exhibit a viscosity of 150 mPa·s to 600 mPa·s, preferably of 200 mPa·s to 550 mPa·s, more especially of 220 mPa·s to 500 mPa·s, especially preferably of 250 mPa·s to 450 mPa·s, and especially of 270 mPa·s to 350 mPa·s, measured according to DIN 53 015 at 75° C.

The compounds (ii-PUR) can be used in mixtures containing chain extension and/or cross-linking agents. The chain extension agents are for the most part 2-functional alcohols with molecular weights of 60 to 499, for example, ethylene glycol, propylene glycol, butandiol-1,4, Pentandiol-1,5, dipropylene glycol, and/or tripropylene glycol. The cross-linking agents are compounds with molecular weights of 60 to 499 and 3 or more active H atoms, preferably, amines, and especially preferably alcohols, for example, glycerine, trimethylolpropane, and/or pentaerythritol.

In a preferred embodiment, the component (ii-PUR) contains (or comprises) 0.25% by weight, preferably, 1 to 20% by weight, of chain-extension and/or cross-linking agents, and 75 to 100% by weight, preferably, 80 to 99% by weight of polyol(s), especially, polyester polyol(s), with reference to the total weight of the component (ii-PUR).

Compounds that accelerate the reaction of the component (i-PUR) with the component (ii-PUR) can be used as catalysts (iii-PUR). For example, tertiary amines and/or organic metal compounds, in particular, in compounds are possible. For example, the following compounds can be used as catalysts: Triethylendiamine, aminoalkyl- and/or aminophenylimidazoles and/or in (II) chlorides of organic carboxylic acids. Catalysts are usually used in the quantity 0.1 to 5% by weight with reference to the weight of the component (ii-PUR).

Suitable gasifying agents (iv-PUR) are generally known compounds with a chemical or physical effect. A preferable physically acting foaming agent is water, which forms carbon dioxide when it reacts with the isocyanate groups. Examples of physical gasifying agents are (cyclo) aliphatic hydrocarbons, preferably those with 4 to 8, especially preferably, 4 to 6, and especially, 5 carbon atoms, partially halogenated hydrocarbons or ether, ketone, or acetate. The quantity of gasifying agent used depends on the required density of the foamed plastic. The various gasifying agents can either be used individually or in any mixtures with each other. Especially preferably, only water is used as a foaming agent, generally in a quantity of 0.1 to 5% by weight, especially, 2.5 to 4% by weight, based on the weight of the component (ii-PUR). Physical foaming agents are preferably used in the quantity <0.5 to −96% by weight, with reference to the weight of the component (ii-PUR).

For the production of polyurethane foamed plastics, in general, the components (i-PUR) and (ii-PUR) are used in such quantities for conversion, that the equivalence ratio of NCO groups to the sum of the reactive hydrogen atoms (especially the sum of the OH groups) corresponds to 1:0.8 to 1:1.25, preferably 1:0.9 to 1:1.15. Herein, a ratio of 1:1 corresponds to an NCO index of 100. The desired open-cell structure of the polyurethane foam is generally assured by a suitable selection of components (i-PUR) to (iv-PUR) known to the specialist. If necessary, after curing, the resulting PUR foamed plastic is reticulated.

The reaction may take place in the presence of (v-PUR) auxiliary and/or additional substances, such as, for example, fillers, cell regulators, cell openers, surface-active compounds and/or stabilizers against oxidative, thermal, or microbial decomposition or aging.

It has also been demonstrated that the tasks named above can be unexpectedly advantageously solved if the polyurethane foamed plastic (c) contains silver in the form of silver ions or in the form of atomic silver. Preferably, a layer of silver is applied after the production of the polyurethane foamed plastic. Alternatively, the silver can already be introduced in the curing compound. Preferably, the polyurethane foamed plastic contains 0.000001 to 0.1% by weight, more preferably, 0.0001 to 0.01% by weight silver, with reference to the total weight of the polyurethane foamed plastic.

It has also been shown that the objects with polyurethane described in the introduction based on merely aliphatic starting materials could not always be achieved successfully. The use of aromatic structural components (i-PUR and/or ii-PUR) is much more advantageous. In a preferable embodiment, therefore, the polyurethane foamed plastic (c) has an aromatic content of 5 to 50%, more preferably, of 10 to 45%, in particular, of 15 to 40%. The aromatic content is determined by the ratio of weight of aromatic rings to the overall weight of the foamed plastic.

Furthermore, this invention relates to an aggregate of a wound support and of a wound dressing that seals the wound space in an essentially vacuum-tight manner and of a connecting device for a suction tube with the characteristics of the associated claims.

The invention therefore further suggests providing an additional fluid feed tube, which projects through the connecting device in such a way that a section of the fluid feed tube is present on the wound-facing side of the support means, which can be used for the direct insertion into the wound space or into the sleeve of the wound support provided there, in order to implement the introduction of fluid directly into the wound space. In this way, the connecting device can be used for vacuum therapy, during which continuously or discontinuously, a fluid, in particular, a liquid or a gas, such as, for example, oxygen, in particular, with pharmaceutically effective substances that support wound healing, can be conveyed to the wound space. The connecting device can therefore be used for so-called instillation therapy. The fluid that is fed via the fluid feed tube can also have an antimicrobial or analgesic effect. However, it can also simply be a rinsing solution, such as, in particular, Ringer's solution. Because the fluid feed tube only opens into the wound space beneath the support means, it can be ensured that the liquid to be conveyed actually reaches the wound space and preferably deep into the wound space and, especially preferably, right down to the base of the wound, where it can have the intended effect. The conveyed liquid and, where applicable, any additional wound fluids or wound exudates are removed via the suction tube by known means and suctioned toward a device generating a vacuum. Facilities for generating a vacuum for the vacuum therapy of wounds, which besides having a device for generating a vacuum also have a single-use container to be thrown away preferably after use, for the collection of body fluids, have been described, in particular, in DE 10 2009 038 130 A1 and DE 10 2009 038 131 A1 of the applicant. Such a facility has a connection for a suction tube leading to the body of the patient as is described here. The features of this facility of the prior art are also included in this application by reference to the previously mentioned applications. The inventive fluid feed tube and a fluid feed facility with which it is combined can either be achieved independently and separately from a facility for generating a vacuum for medical applications, for example, in the form of an instillation device, or the fluid feed facility can be integrated into the mentioned facility for generating a vacuum.

According to a preferred embodiment of the inventive connecting device it has proved advantageous if the fluid feed tube extends parallel to the suction tube at least in the region of the connecting device. This simplifies attachment on the vacuum dressing but also the disposition and placement of the conduits around the patient. Irrespective of this, it also proves practical if the conduits extend parallel in the region of the support means.

It may be noted at this point that the two-dimensional vacuum-tight and flexible support means for the suction tube and consequently also for the fluid feed tube is a two-dimensionally constituted interface between the suction tube and the vacuum dressing. The support means together with the suction tube and the additionally brought in fluid feed tube constitutes a flat, flexible, and two-dimensional configuration. Viewed from above, at least, the support means is constituted with more overlap two-dimensionally than the suction tube connected to it and the additionally brought in fluid feed tube. As a result, the support means forms a larger connecting area with the upper surface of the vacuum dressing facing away from the wound.

Further characteristics, details, and advantages can be derived from the appended claims and from the following description of a preferred embodiment of an inventive wound support and its use in the vacuum therapy of wounds. The drawing shows:

DESCRIPTION OF THE PREFERRED EMBODIMENT

Figure 1:
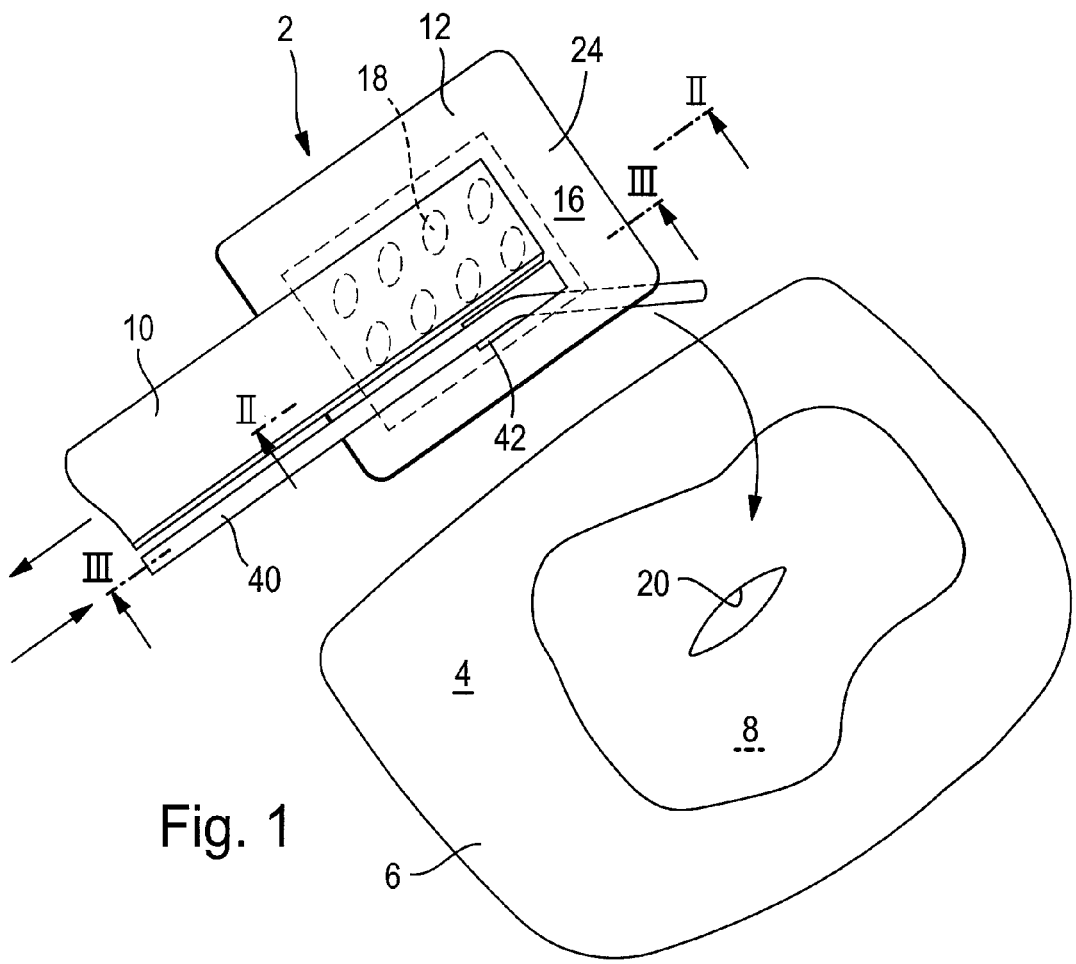
FIG. 1 a perspective view, not true to scale, of an connecting device for use in the vacuum therapy of wounds, as well as an indicated wound with a vacuum dressing.
Figure 2:
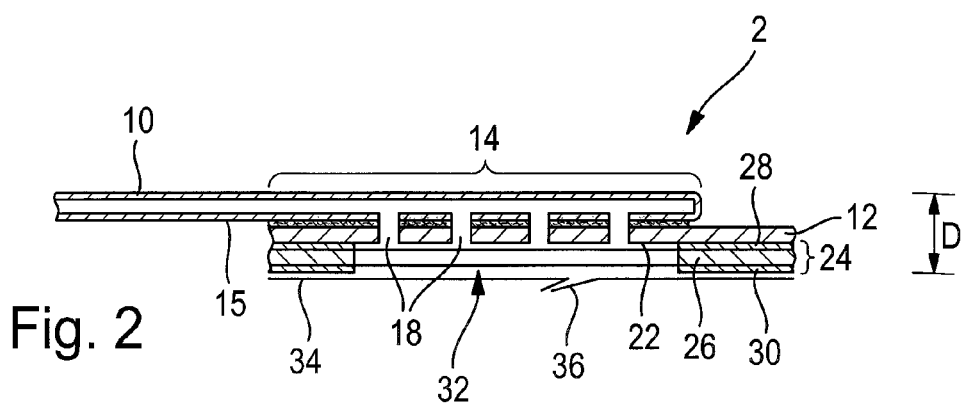
FIG. 2 a schematic sectional view, not true to scale, of the connecting device according to FIG. 1 with a sectional plane II-II.

The figures show different views of a connecting device overall designated with the reference sign 2 for use in the vacuum treatment of wounds. The illustrated connecting device 2 is applied to an upper side 4, facing away from the wound, of a schematic vacuum dressing 6, which overlaps a wound 8 to be treated, which seals vacuum tight with respect to the atmosphere and which is fixed by adhesive means in a way still to be described.

The connecting device 2 comprises a flat conduit shown as an example in the illustration, in the shape of a suction tube 10 made of an elastomer flexible material and a two-dimensionally extending, plate-shaped support means 12, which holds and supports the flat suction tube 10, so that the pressure and torsional forces applied to the suction tube 10 are introduced evenly into the large-area support means 12 and can be taken up by the latter.

The suction tube 10 is sufficiently flat that in a longitudinal end section 14, preferably almost 100% of its surface which is projected onto the support means 12 is connected to the support means 12. The relevant flat side 15 of the suction tube 10 can be adhesively fixed or vulcanized, that is, thermally joined, onto the upper side 16, facing away from the wound, of the support means 12.

Preferably, after vacuum-tight joining of the suction pipe 10 with support means 12, openings 18 that pass through the support means 12 and through the suction pipe 10 are formed, which communicate with a schematically shown opening 20 or multiple openings 20 in the vacuum dressing 6 when the connecting device 2 is applied to the vacuum dressing 6, in order to apply a vacuum to the wound space.

The extension of the thickness D of the combination of the suction pipe 10 and support means 12 is no more than 7 mm, preferably, no more than 5 mm, and further, preferably only 3 to 4 mm.

Furthermore, the figures also show that the connecting device 2 has an adhesion layer 24 on the wound-facing side 22 of the support means 12. By means of this adhesion layer 24, the connecting device 2 can be adhesively fixed to the upper side 4, facing away from the wound, of the vacuum dressing 6. The adhesion layer 24 is constituted as three layers and comprises a middle support layer 26, a first adhesive layer 28 held on the support layer 26 and facing the support means 12, and a second adhesive layer 30 held on the support layer 26, facing away from the support means 12, that is, facing the vacuum dressing 6. In the preferred case shown in the example, all three layers of the adhesion layer 24 are constituted such that they are coextensive. The adhesion layer 24 is, in its entirety, cut in lengths and/or punched out from a flat material coated on both sides with adhesive material. In the illustrated example, it is frame shaped, that is, it extends continuously around the circumference and extends around the central section 32 of the support means 12 into which the schematically illustrated openings 18 of the support means 12 and/or the suction pipe 10 open in the direction of the vacuum dressing 6. The adhesive surface of the first and the second adhesive layers 28, 30 in the illustrated example is only approx. 30 cm$^2$ in size. However, it is also expressly mentioned at this stage that the adhesion layer 24 can also extend across the entire wound-facing side 22 of the support means 12, wherein accordingly, the openings 18 in the support means 12 and/or in the suction pipe 10 must exhibit aligned or communicating through-openings. The adhesive surface is then only approx. 40 cm$^2$.

The adhesive layers 28 and 30 are made of varying adhesive materials, which are correspondingly optimized to the materials of the support means 12 and/or of the vacuum dressing 6. If, for example, the support means 12 is made of silicone, it is recommended that the first adhesive layer 28 comprise a silicone adhesive. If the vacuum dressing 6 for which the connecting device 2 is conceived is made of polyurethane and/or is constituted with an upper side 4, facing away from the wound, made of polyurethane, it is recommended that the second adhesive layer 30 comprise an acrylate adhesive which adheres particularly well to polyurethane. By using the inventive adhesion layer 24 it is quite possible to match both these adhesive layers 28 and 30 optimally to the materials of the support means 12 and/or of the vacuum dressing 6 with which they are adhesively combined and manufactured in this combination.

The second adhesive layer 30 is further surrounded by a two-part removable protective layer 34, which has a handling tongue 36 for removing both parts.

Figure 3:
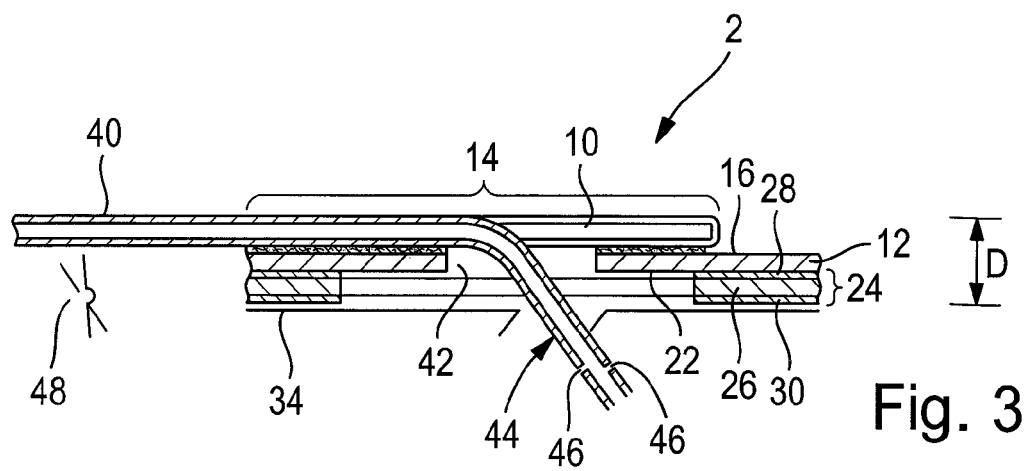
FIG. 3 a schematic sectional view, not true to scale, of the connecting device according to FIG. 1 with sectional plane III-III.

FIGS. 1 and 3 further show a fluid feed tube 40 with which a fluid can be introduced to the wound space, for example, to rinse or instill the wound. The fluid feed tube 40 is preferably conveyed to the support means 12 in the same plane as the suction tube 10 and parallel with the suction tube 10; it is also held by the support means 12 and is permanently joined to the upper side 16, facing away from the wound, of the support means 12, for example, using adhesive or by material bonding. Inventively, the fluid feed tube 40 extends through a further opening 42 in the support means 12 toward the wound-facing side 22 of the support means 12 and there protrudes at an acute angle toward the wound. Because the fluid feed tube 40 is made of a flexible material in the way described in the introduction, a protruding end section 44 of the fluid feed tube 40 can easily and essentially without resistance bend in another desired direction and be oriented with respect to the wound and/or the wound support in a way yet to be described. Additional transverse openings 46, which are merely schematically shown, can be constituted in the wall of the protruding end section 44 of the fluid feed tube 40 for specific applications. Furthermore, a disconnection device 48 is schematically shown with which the cross-section of the fluid feed tube 40 can be reduced to zero.

Figure 4:
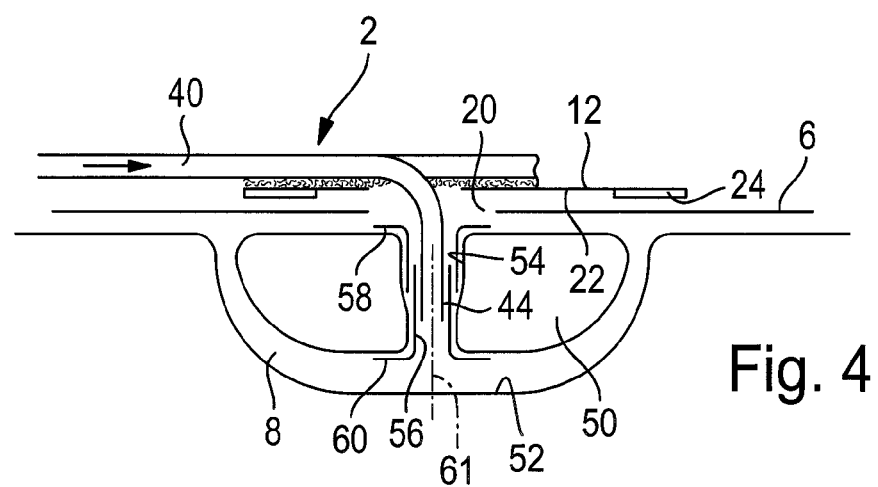
FIG. 4 a schematic sectional view, not true to scale, of the connecting device in combined operation with an inventive wound support.

FIG. 4 very schematically shows the application of the connecting device 2 together with an inventive wound support 50 on a wound 8, which is sealed with a vacuum dressing 6 leaving only opening 20 free.

In the region of this opening 20 in vacuum dressing 6, the connecting device is applied sealingly, in particular, by means of the mentioned adhesion layer 24. Alternatively, the connecting device 2 could be fixed by additional adhesive film that overlaps the connecting device 2 or by sealing the same at the upper side 16, facing away from the wound, of the support means 12. The schematic cross-section of FIG. 4 shows only the sectional plane through the fluid feed tube 40. It shows how the end section 44 of the fluid feed tube 40 protruding from the wound-facing side 22 of the support means 12 is introduced into the wound support 50 in the direction of the wound base 52. Inventively, a through-hole 54 is constituted for this in the wound support 50. A sleeve 56 is disposed in the through-hole 54. The sleeve 56 is constituted as two sleeve parts 58, 60, that are inserted through the through-hole from opposing sides of the wound support 50. The sleeve parts 58, 60 extend toward each other in a telescopic manner along a sleeve longitudinal axis 61. In this way, the sleeve length can be set automatically according to the deformation of the wound support 50. Depending on the vacuum and compression of a wound support 50, preferably formed from absorbent foam, the sleeve length can be set automatically. The sleeve 58 guides the end section 44 of the fluid feed tube 40 and prevents the latter from resting against the wound base 52. In this way, liquid can be conveyed via the fluid feed tube 40 to deep regions of the wound 8, preferably down to the wound base 52. The introduced liquid can then be removed together with wound fluids via the suction tube 10 not illustrated in FIG. 4.

FIGS. 5a to f show various purely schematic representations of inventive wound supports 50, whose geometry can only be understood in a simplified and schematic form.

Each of the wound supports 50 is made of a flexibly compliant foam material, preferably in the way described in detail above. In the embodiment according to FIG. 5a, the sleeve 56 is constituted cylindrically and inserted through the through-hole 54 of the wound support 50. If can, for example, be held by friction contact in the through-hole 54 in direct contact with the foamed material of the wound support 50.

Figure 5A:
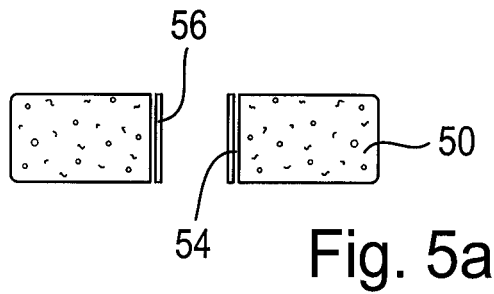
FIG. 5 schematic representations of inventive wound supports.
Figure 5B:
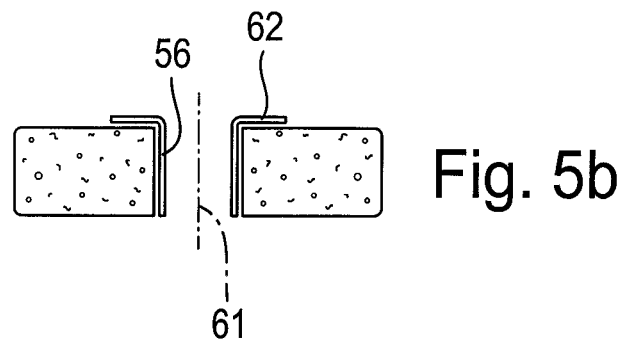

In the case of the wound support according to FIG. 5b, the sleeve 56 has a bent out collar 62 at one end, as do the sleeve parts 58, 60 according to FIG. 4, which, with reference to the sleeve longitudinal axis 61, forms an axial connection with the foamed material. The collar 62 is preferably joined to the other cylindrical part of the sleeve 56 to form one piece.

Figure 5C:
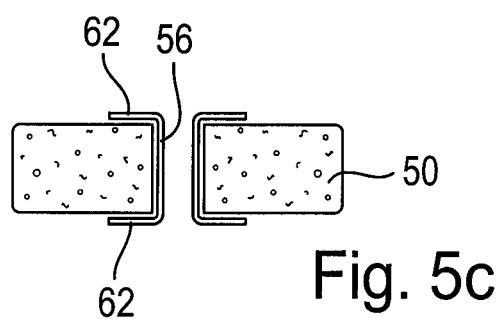
Figure 5D:
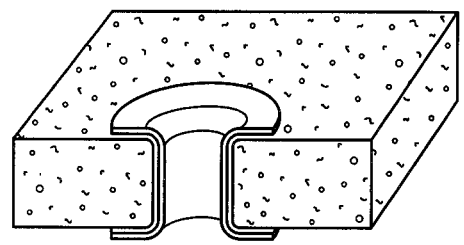

In the embodiment according to FIG. 5c, the sleeve 56 has one such a collar 62 at each end. This creates a reception space between the bands 62 for the foamed material of the wound support 50, so that the sleeve 56 is held to the wound support 50 by positive action to a certain degree. FIG. 5d shows this in a perspective view.

Figure 5E:
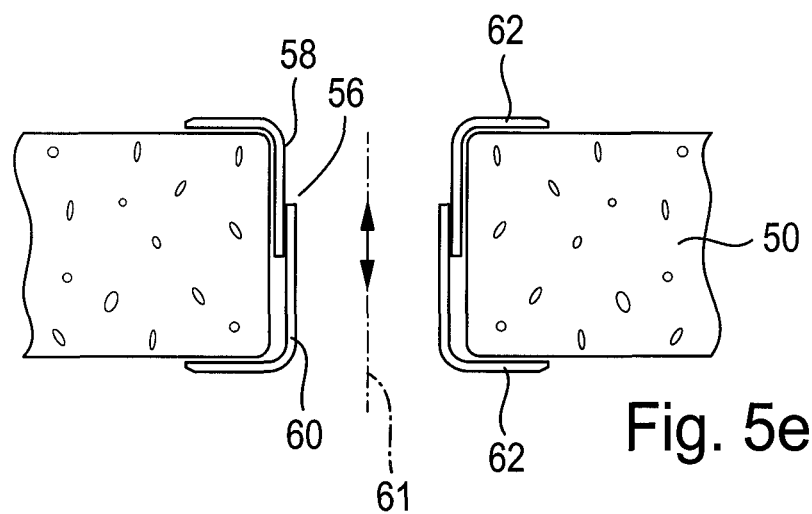
Figure 5F:
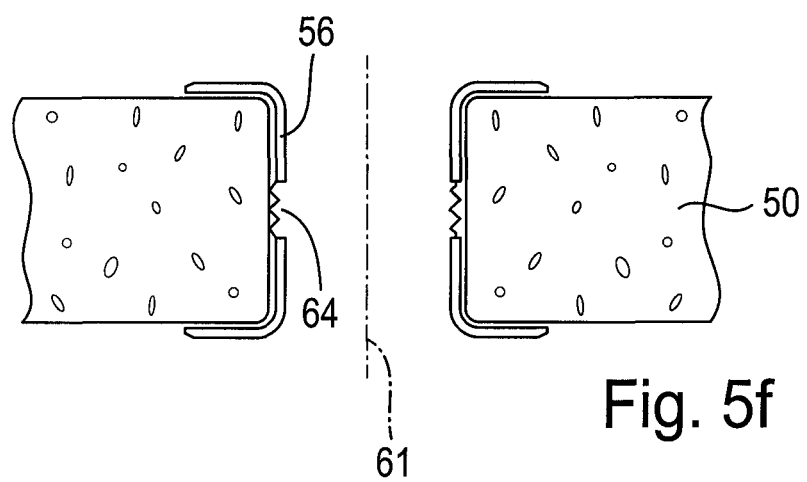

In the embodiment according to FIG. 5e, a sleeve 56 is formed from two sleeve parts 58, 60 (as in FIG. 4), each of which has a collar 62 and which can slide telescopically toward each other along the sleeve longitudinal axis 61. The sleeve parts 58, 60 can therefore automatically adapt themselves to the deformation of the wound support 50. FIG. 5*f* shows another embodiment in which the two sleeve parts 58, 60, can be moved by means of a bellows-type coupling along the sleeve longitudinal axis.

We claim:

1. A device for vacuum therapy of a wound, the device comprising:
    a vacuum dressing that seals the wound space in an essentially vacuum-tight manner;
    a connecting device, said connecting device having a suction tube to which a vacuum can be applied and a two-dimensional vacuum-tight, flexible support means for the suction tube, said support means being structured for application, in an essentially vacuum-tight manner, to said vacuum dressing, wherein said vacuum dressing overlaps and seals the wound with respect to atmosphere such that said suction tube communicates with the wound space through at least one opening in said support means and in said vacuum dressing;
    a wound support disposed beneath said vacuum dressing in the wound space, wherein the wound support comprises a flexibly compliant foamed material having through-hole that extends in a direction of a wound depth and a sleeve disposed in said through-hole, said sleeve having a collar on one side or on both sides of said foamed material, said collar resting axially against a side of said foamed material that surrounds said through-hole with respect to a longitudinal axis of said sleeve; and
    a fluid feed tube, said fluid feed tube structured for introducing a fluid medium to the wound space in order to promote healing of the wound, said fluid feed tube disposed in a same plane as said suction tube and fed to said support means, said fluid feed tube having a thickness which does not exceed a thickness of said suction tube, wherein said fluid feed tube is passed, in a sealed manner, through an opening in said support means to protrude beyond a wound-facing side of said support means and to project through an opening in said vacuum dressing into said sleeve, said sleeve thereby being disposed, structured and dimensioned to guide an end section of said fluid feed tube for conveying liquid through said fluid feed tube into deep regions of the wound without having an end section of said fluid feed tube rest against a base of the wound.

2. The device of claim 1, wherein said sleeve rests directly against said foamed material of the wound support.

3. The device of claim 1, wherein said collar is closed around an entire circumference thereof.

4. The device of claim 1, wherein said sleeve has an adjustable length, said adjustable length adapting said sleeve to a compression or contraction of said foamed material.

5. The device of claim 1, wherein said sleeve comprises two telescopic sleeve sections that slide toward each other along a longitudinal axis of said sleeve.

6. The device of claim 1, wherein said sleeve comprises two sleeve parts that are moved toward each other by means of a bellows-type coupling along a longitudinal axis of said sleeve.

7. The device of claim 1, wherein said flexibly compliant foamed material comprises or consists essentially of an open-cell polyurethane foamed plastic, obtained by conversion of a mixture containing components selected from the group consisting of:
    (i) polyisocyanate in MDI, PMDI, and/or TDI
    (ii) polyol or polyesterpolyol,
    (iii) a gasifying agent, and
    (iv) a catalyst,
wherein, following three days of storage in bovine serum, said open-cell foamed plastic exhibits a tensile strength, measured according to DIN 53571, of between 80 kPa and 300 kPa or of between 150 kPa and 220 kPa.

8. The device of claim 7, wherein said polyol is polyesterpolyol.

9. The device of claim 8, wherein said polyesterpolyol is obtained by reaction of a dicarboxylic acid containing 4 to 8 carbon atoms with a dialcohol containing 2 to 6 carbon atoms.

10. The device of claim 7, wherein said open-cell polyurethane foamed plastic exhibits an elongation at break of 250% to 650% or of 260 to 320%, measured according to DIN 53571.

11. The device of claim 7, wherein said open-cell polyurethane foamed plastic has an air permeability of 1000 to 8000 $1/(m^2 \, sec)$ or of 2400 to 3300 $1/(m^2 \, sec)$, measured according to DIN EN ISO 9237.

12. The device of claim 7, wherein said open-cell polyurethane foamed plastic has a bulk density of between 15 and 30 $kg/m^3$ or between 24 and 28 $kg/m^3$, measured according to DIN EN ISO 845.

13. The device of claim 7, wherein said open-cell polyurethane foamed plastic has an aromatic content of 5 to 50% or of 15 to 40%.

14. The device of claim 1, wherein said suction tube is constituted to be flexible and flat and is, in its intended use, non-detachably and two-dimensionally connected to said support means in a wound-side longitudinal section with at least 70% of a surface thereof projected perpendicularly onto said support means, wherein said support means and said suction tube are mutually parallel with main planes thereof resulting from flat shapes thereof, and wherein a combined thickness of said suction tube and said support means does not exceed 7 mm.

15. The device of claim 1, wherein an at least three-layer adhesion layer is disposed on a wound-facing side of said support means, said adhesive layer having a middle support layer, a first adhesive layer held on said support layer and facing said support means, and a second adhesive layer held on said support layer and facing away from said support means, wherein said adhesive layer does not block said at least one opening in said support means.

16. A device for vacuum therapy of a wound, the device comprising:
    a vacuum dressing that seals the wound space in an essentially vacuum-tight manner;
    a connecting device, said connecting device having a suction tube to which a vacuum can be applied and a two-dimensional vacuum-tight, flexible support means for the suction tube, said support means being structured for application, in an essentially vacuum-tight manner, to said vacuum dressing, wherein said vacuum dressing overlaps and seals the wound with respect to atmosphere such that said suction tube communicates with the wound space through at least one opening in said support means and in said vacuum dressing;
    a wound support disposed beneath said vacuum dressing in the wound space, wherein the wound support comprises a flexibly compliant foamed material having a through-hole that extends in a direction of a wound depth and a sleeve disposed in said through-hole, wherein said sleeve has an adjustable length, said adjustable length adapting said sleeve to a compression or contraction of said foamed material; and
    a fluid feed tube, said fluid feed tube structured for introducing a fluid medium to the wound space in order to promote healing of the wound, said fluid feed tube disposed in a same plane as said suction tube and fed to said support means, said fluid feed tube having a thickness which does not exceed a thickness of said suction tube, wherein said fluid feed tube is passed, in a sealed manner, through an opening in said support means to protrude beyond a wound-facing side of said support means and to project through an opening in said vacuum dressing into said sleeve, said sleeve thereby being disposed, structured and dimensioned to guide an end section of said fluid feed tube for conveying liquid through said fluid feed tube into deep regions of the wound without having an end section of said fluid feed tube rest against a base of the wound.

* * * * *